US010185926B2

United States Patent
Utech et al.

(10) Patent No.: US 10,185,926 B2
(45) Date of Patent: Jan. 22, 2019

(54) COMPONENT BASED AGGREGATION OF MEDICATION ORDERS

(71) Applicant: CareFusion 303, Inc., San Diego, CA (US)

(72) Inventors: Thomas William Utech, Dallas, TX (US); Maria Consolacion Jaskela, San Rafael, CA (US); William Lee Webster, Rockwall, TX (US)

(73) Assignee: CareFusion 303, Inc., San Diego, CA (US)

( * ) Notice: Subject to any disclaimer, the term of this patent is extended or adjusted under 35 U.S.C. 154(b) by 779 days.

(21) Appl. No.: 14/742,577

(22) Filed: Jun. 17, 2015

(65) Prior Publication Data

US 2015/0286985 A1    Oct. 8, 2015

Related U.S. Application Data

(63) Continuation of application No. 13/901,497, filed on May 23, 2013, now Pat. No. 9,076,115, which is a
(Continued)

(51) Int. Cl.
*G06Q 10/08* (2012.01)
*G06Q 10/06* (2012.01)
(Continued)

(52) U.S. Cl.
CPC .......... *G06Q 10/087* (2013.01); *G06F 19/00* (2013.01); *G06F 19/3462* (2013.01);
(Continued)

(58) Field of Classification Search
CPC ........ G06Q 50/22; G06Q 50/24; G06F 17/00; G06F 19/30; G06F 19/34; G06F 19/3456;
(Continued)

(56) References Cited

U.S. PATENT DOCUMENTS 4,653,010 A * 3/1987 Figler ..................... A61J 3/002
222/134
5,208,762 A * 5/1993 Charhut ................ A61J 7/0084
221/9
(Continued)

FOREIGN PATENT DOCUMENTS

CN    102473173 A    5/2012
CN    102483773 A    5/2012
(Continued)

OTHER PUBLICATIONS

Mexican Office Action dated Sep. 6, 2017 from Mexican Patent Application No. MX/a/2015/016010, 7 pages.
(Continued)

*Primary Examiner* — Jason S Tiedeman
(74) *Attorney, Agent, or Firm* — Morgan, Lewis & Bockius LLP

(57) ABSTRACT

A system for component based aggregation of medication orders may include a processor and memory. The processor may receive display a queue that lists medication orders to be prepared by a healthcare professional, the medication orders indicating component medications that will be used to prepare the ordered medications. The processor may receive a selection of a first medication order listed in the queue, where the first medication order indicates a first component medication. The processor may determine a second medication order listed in the queue that indicates the first component medication. The processor may reorder the displayed queue such that the second medication order is listed adjacent to the first medication order. The processor may notify the healthcare professional of the second medication order, such as by displaying an indication of the second medication order separately from the queue.

20 Claims, 6 Drawing Sheets

Related U.S. Application Data continuation-in-part of application No. 13/754,724, filed on Jan. 30, 2013, now Pat. No. 9,342,484.

(51) Int. Cl.

| | | |
|---|---|---|
| *G06Q 50/22* | (2018.01) | |
| *G16H 40/60* | (2018.01) | |
| *G16H 20/13* | (2018.01) | |
| *G06F 19/00* | (2018.01) | |
| *H04L 29/08* | (2006.01) | |

(52) U.S. Cl.
CPC .............. *G06Q 10/06* (2013.01); *G06Q 50/22* (2013.01); *G16H 20/13* (2018.01); *G16H 40/60* (2018.01); *H04L 67/12* (2013.01)

(58) Field of Classification Search
CPC . G06F 19/3462; G06F 19/3468; G16H 20/00; G16H 20/13; G16H 20/17; A61J 7/0076; A61J 7/0084
USPC ...... 705/2, 3, 7.12–7.27; 235/375, 376, 381; 700/8, 32, 95, 103, 106, 213, 214, 216, 700/219, 223, 231
See application file for complete search history.

(56) References Cited

U.S. PATENT DOCUMENTS

| | | | |
|---|---|---|---|
| 5,991,728 | A | 11/1999 | DeBusk et al. |
| 6,202,923 | B1 | 3/2001 | Boyer et al. |
| 6,317,719 | B1 | 11/2001 | Schrier et al. |
| 7,111,780 | B2 | 9/2006 | Broussard et al. |
| 7,349,858 | B1 | 3/2008 | McGrady et al. |
| 7,734,478 | B2 | 6/2010 | Goodall et al. |
| 7,860,724 | B2 | 12/2010 | Chudy et al. |
| 8,195,328 | B2 | 6/2012 | Mallett et al. |
| 8,280,550 | B2 | 10/2012 | Levy et al. |
| 8,560,345 | B2 | 10/2013 | Wehba et al. |
| 8,627,639 | B2 * | 1/2014 | Ali .......................... B65B 5/103 53/473 |
| 8,655,751 | B2 * | 2/2014 | Renz ................. G06Q 10/0875 119/51.01 |
| 8,688,468 | B1 | 4/2014 | daCosta et al. |
| 9,342,484 | B2 | 5/2016 | Utech et al. |
| 2002/0013640 | A1 | 1/2002 | Phoon et al. |
| 2002/0143434 | A1* | 10/2002 | Greeven ............. G06F 19/3418 700/236 |
| 2002/0198624 | A1 | 12/2002 | Greenwald et al. |
| 2003/0189058 | A1* | 10/2003 | Liff ..................... G06F 19/3462 221/13 |
| 2003/0195654 | A1* | 10/2003 | Spano, Jr. ........... G06F 19/3462 700/237 |
| 2004/0078231 | A1 | 4/2004 | Wilkes et al. |
| 2004/0088187 | A1* | 5/2004 | Chudy ................... G06Q 10/10 705/2 |
| 2006/0149416 | A1 | 7/2006 | Mohapatra et al. |
| 2006/0200369 | A1 | 9/2006 | Batch et al. |
| 2006/0249423 | A1 | 11/2006 | Reijonen |
| 2008/0195246 | A1 | 8/2008 | Khan et al. |
| 2008/0195416 | A1* | 8/2008 | Tribble ................. G06Q 10/10 705/2 |
| 2009/0012813 | A1 | 1/2009 | Berzansky et al. |
| 2009/0272677 | A1 | 11/2009 | Mallett et al. |
| 2010/0042437 | A1 | 2/2010 | Levy et al. |
| 2010/0094653 | A1* | 4/2010 | Tribble ................. G06F 19/326 705/3 |
| 2010/0161113 | A1 | 6/2010 | Tribble et al. |
| 2010/0174552 | A1 | 7/2010 | Hawkes et al. |
| 2010/0241270 | A1* | 9/2010 | Eliuk ........................ A61J 1/20 700/216 |
| 2011/0010196 | A1* | 1/2011 | Nee ..................... G06F 19/3456 705/3 |
| 2011/0184751 | A1* | 7/2011 | Holmes ............... G06F 19/3462 705/2 |
| 2012/0173254 | A1* | 7/2012 | Korhnak ................ G06Q 10/06 705/2 |
| 2012/0185277 | A1 | 7/2012 | Tribble et al. |
| 2012/0239422 | A1* | 9/2012 | Chudy ................ G06F 19/3462 705/2 |
| 2012/0323602 | A1* | 12/2012 | Ryan .................. G06F 19/3456 705/3 |
| 2013/0018356 | A1 | 1/2013 | Prince et al. |
| 2013/0262138 | A1* | 10/2013 | Jaskela .................. G06Q 50/22 705/2 |
| 2014/0156294 | A1* | 6/2014 | Tribble ................. G06F 19/326 705/2 |
| 2014/0180475 | A1* | 6/2014 | Paradissis ............ G06Q 10/087 700/241 |

FOREIGN PATENT DOCUMENTS

| | | | | |
|---|---|---|---|---|
| EP | 1656988 A1 * | 5/2006 | .......... | B01F 13/1055 |
| KR | 20120070045 A | 6/2012 | | |
| WO | WO-0023908 A1 | 4/2000 | | |
| WO | WO-200139874 | 6/2001 | | |
| WO | WO-2006060572 A1 | 6/2006 | | |

OTHER PUBLICATIONS

Extended European Search Report for Application No. 14801251.1, dated Jan. 16, 2017, 8 pages.
Memo for Mexican Office Action for Application No. MX/a/2015/016010, memo dated Apr. 4, 2017, 3 pages.
Chinese Office Action for Application No. 201480017522.0, dated Mar. 20, 2017, 12 pages.
Anonymous: "Pyxis MedStation ™ 4000 System. Console User Guide" In: "Part No. 127157-06", Nov. 1, 2010, Cardinal Health, XP055121062, pp. 1-228, p. 21-22, p. 38-61, p. 123-124, p. 157-166, p. 200, p. 216.
"Dose Edge Pharmacy Workflow Manager," Baxter International Inc., visited May 21, 2015, retrieved from <https://btsp.baxa.com/doseedge/>.
International Search Report and Written Opinion in International Patent Application No. PCT/US2014/012594 dated Jun. 11, 2014, 16 pages.
International Search Report and Written Opinion in PCT Patent Application No. PCT/US2014/039228 dated Aug. 22, 2014, 11 pgs.
International Search Report and Written Opinion in PCT Application No. PCT/US2014/038654 dated Oct. 7, 2014, 12 pages.

* cited by examiner

FIG. 4

COMPONENT BASED AGGREGATION OF MEDICATION ORDERS

CROSS-REFERENCE TO RELATED APPLICATIONS

This application is a continuation of U.S. patent application Ser. No. 13/901,497, entitled "COMPONENT BASED AGGREGATION OF MEDICATION ORDERS," filed on May 23, 2013 which is a continuation-in-part of U.S. patent application Ser. No. 13/754,724, entitled "VARIABLE DOSE DISPENSING SYSTEM," filed Jan. 30, 2013, both of which are expressly incorporated by referenced herein.

TECHNICAL FIELD

The present description relates generally to aggregation of medication orders, and more particularly, but not exclusively, to component based aggregation of medication orders.

BACKGROUND

A healthcare facility, such as a hospital, may include a pharmacy that receives patient orders for medications, e.g. from a physician order entry system, and formulates the ordered medications for administration to patients. For example, a healthcare professional in the pharmacy, such as a pharmacy technician, may formulate ordered medications, such as ordered intravenous (IV) medications, in the order in which the orders for the medications are received. An order for a medication may generally indicate one or more component medications used to formulate the ordered medication. Thus, the pharmacy technician may retrieve containers of the component medications that are indicated on the order and may use the retrieved containers of the component medications to formulate the ordered medication. A retrieved container may be used to formulate one or more ordered medication. If there is any excess component medication left in the retrieved containers after formulating the ordered medication, the excess component medications may be disposed of by the healthcare professional per hospital protocol. With the high costs of medications, any reduction in wastage can lead to significant cost savings.

SUMMARY

The disclosed subject matter relates to a method for component based aggregation of medication orders. The method may include receiving a plurality of medication orders, at least some of the plurality of medication orders indicating a first component medication or a second component medication to be formulated into a medication for delivery. The method may further include aggregating, from the plurality of medication orders, a first batch of medication orders that each indicate the first component medication and a second batch of medication orders that each indicate the second component medication. The method may further include determining a first amount of the first component medication to be used to formulate the first batch of medication orders and a second amount of the second component medication to be used to formulate the second batch of medication orders. The method may further include indicating the first amount of the first component medication and the second amount of the second component medication to be used to formulate the first batch of medication orders and the second batch of medication orders, respectively.

The disclosed subject matter also relates to a system for component based aggregation of medication orders. The system includes one or more processors and a memory including instructions that, when executed by the one or more processors, cause the one or more processors to: display a queue listing a plurality of medication orders to be prepared, each of the plurality of medication orders indicating one of a plurality of component medications, receive a selection of a first medication order of the plurality of medication orders listed in the queue, wherein the first medication order of the plurality of medication orders indicates a first component medication of the plurality of component medications, determine a second medication order of the plurality of medication orders listed in the queue that indicates the first component medication of the plurality of component medications, and reorder the displayed queue such that the second medication order of the plurality of medication orders is listed adjacent to the first medication order of the plurality of medication orders.

The disclosed subject matter also relates to a machine-readable medium embodying instructions that, when executed by a machine, allow the machine to perform a method for component based aggregation of medication orders. The method may include receiving a plurality of medication orders to be prepared, each of the plurality of medication orders indicating one of a plurality of component medications. The method may further include receiving an indication that a medication order of the plurality of medication orders is being prepared by a healthcare professional, wherein the medication order of the plurality of medication orders indicates a first component medication of the plurality of component medications. The method may further include determining other medication orders of the plurality of medication orders that indicate the first component medication of the plurality of component medications. The method may further include displaying the other medication orders of the plurality of medication orders that indicate the first component medication of the plurality of component medications.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

Certain features of the subject technology are set forth in the appended claims. However, for purpose of explanation, several embodiments of the subject technology are set forth in the following figures.

FIG. 4 illustrates an example user interface that may be utilized in a system for component based aggregation of medication orders in accordance with one or more embodiments.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more embodiments. In one or more instances, well-known structures and components are shown in block diagram form in order to avoid obscuring the concepts of the subject technology.

The subject system for component based aggregation of medication orders may allow a healthcare facility, such as a hospital, to substantially minimize the amount of medication that is wasted when component medications are picked, or retrieved, by a healthcare professional, for the purposes of preparing ordered medications. For example, the subject system may provide a healthcare professional with an indication of a container, or a set of containers, that provides a sufficient amount of the component medication to prepare the ordered medications while minimizing any excess amount of the component medication, e.g. any amount of the component medication that is left unused after the ordered medications are prepared. Furthermore, the subject system may allow a healthcare facility to minimize the amount of component medications that are wasted when ordered medications are prepared. For example, the subject system may aggregate medication orders, also referred to as orders or orders for medications, based on common component medications such that a healthcare professional can sequentially prepare ordered medications that have a common component medication. In this manner, the likelihood of any component medication being wasted, or expiring, is substantially minimized.

Figure 1:
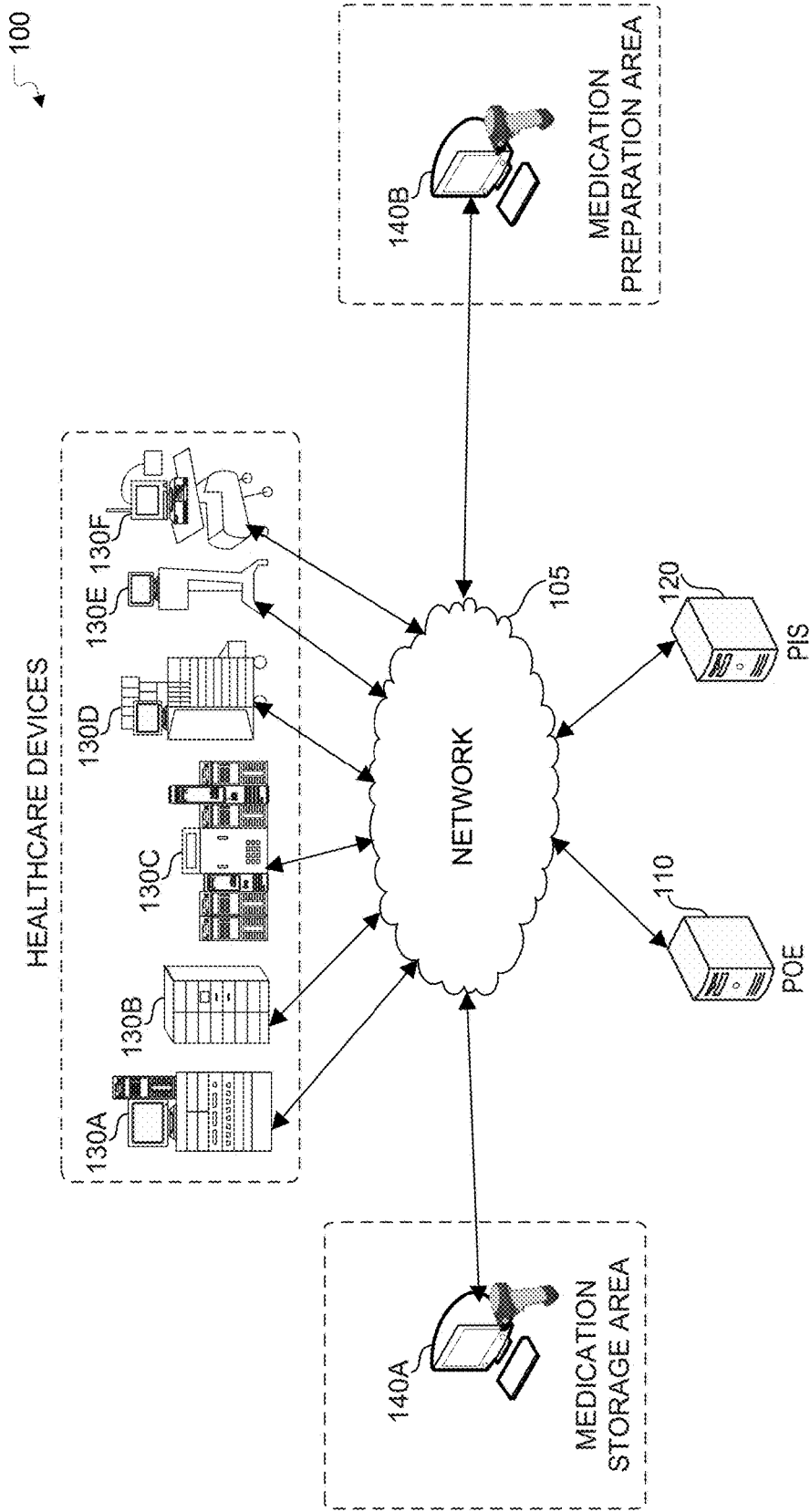
FIG. 1 illustrates an example hospital network environment in which a system for component based aggregation of medication orders may be implemented in accordance with one or more embodiments.

FIG. 1 illustrates an example hospital network environment 100 in which a system for component based aggregation of medication orders may be implemented in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The example hospital network environment 100 includes a network 105, a physician order entry (POE) system 110, a pharmacy information system (PIS) 120, one or more healthcare devices 130A-F, an electronic device 140A that is located in a medication storage area, and an electronic device 140B that is located in a medication preparation area. In one or more embodiments, the medication storage area may be an area where a medication inventory of a healthcare facility is stored, and the medication preparation area may be an IV workroom or compounding station, such as a clean workroom, a sterile workroom, and/or a non-sterile workroom. Other types of medication storage areas and/or medication preparation areas are also possible, such as nurse stations.

The POE system 110, PIS 120, healthcare devices 130A-F, and/or electronic devices 140A-B may be communicatively coupled to one another, such as by the network 105. In one or more embodiments, one or more of the POE system 110, the PIS 120, the healthcare devices 130A-F, or the electronic devices 140A-B may be directly coupled to one another. In addition, there may be a number of other devices connected to the network 105, such as a control system, additional healthcare systems, e.g. a hospital information system (HIS), a laboratory information system (LIS), or other clinical and/or logistical systems, additional healthcare devices, additional electronic devices, external systems, computing devices, mobile devices, etc. The POE system 110, the PIS 120, one or more of the healthcare devices 130A-F, and/or one or more of the electronic devices 140A-B may be, or may include all or part of, the electronic system that is discussed further below with respect to FIG. 6.

The network 105 may be a communication network, such as a public communication network (such as the Internet, cellular data network, dialup modems over a telephone network), a private communications network (such as private local area network ("LAN"), leased lines), etc. The network 105 may also include, but is not limited to, any one or more of the following network topologies, including a bus network, a star network, a ring network, a mesh network, a star-bus network, a tree or hierarchical network, and the like. The connections of the network 105 may be wired or wireless. For example, one or more of the POE system 110, the PIS 120, the healthcare devices 130A-F, and/or the electronic devices 140A-B may transmit wireless signals over the network 105, such as wireless Ethernet signals, radio frequency (RF) signals, infrared (IR) signals, Bluetooth signals, or any other means capable of carrying information in a wireless manner between devices having appropriate transmitters and/or receivers.

The POE system 110 and/or the PIS 120 may be single computing devices, such as computer servers. Alternatively, the POE system 110 and/or the PIS 120 may represent one or more computing devices (such as a cloud of computers and/or a distributed system) that are communicatively coupled, such as communicatively coupled over the network 105, and that collectively, or individually, perform one or more functions that can be performed server-side, such as receiving messages, transmitting messages, storing messaging, receiving control commands, providing user interfaces, transmitting notifications, etc. The POE system 110 and/or the PIS 120 may be coupled with various databases, such as data stores, storage services, or other computing devices.

The POE system 110 and/or the PIS 120 may be systems that facilitate with providing healthcare, and/or provide healthcare. The POE system 110 may be used, for example, by physicians to enter orders for patients, such as orders for medications to be administered to patients. The orders for medications may be transmitted to the PIS 120 for preparation. The PIS 120 may store, for example, information pertaining to a pharmacy of a healthcare facility, such as outstanding orders, filled orders, medication inventory, patient medical profiles/histories, etc. For example, the PIS 120 may be coupled to a database that stores, e.g., an inventory of the medications that are stored in the medication storage area and/or medications that are temporarily stored in one or more medication preparation areas.

The healthcare devices 130A-F may include infusion devices, such as infusion pumps, drug delivery devices, dispensing devices, such as automated dispensing machines, monitoring devices, respiratory devices, such as ventilators, waste devices, such as drug disposal devices, or generally any device that may facilitate with providing healthcare and/or may provide healthcare. One or more of the healthcare devices 130A-F may include a processor and/or a memory. Alternatively, or in addition, one or more of the healthcare devices 130A-F may be communicatively coupled to a device that includes a processor and a memory, such as via a serial port.

For example, the healthcare devices 130A-F may include automated dispensing machines (ADM), such as Pyxis Medstations™, which store and dispense medications at nurse's stations, thereby providing distributed access to medications. The healthcare devices 130A-F may further include infusion devices, such as infusion pumps, that assist with administering medications to patients. The healthcare devices 130A-F may also include waste devices that accept and store wasted medications, e.g. excess medications, from healthcare professionals and track the amount of medications wasted by healthcare professionals. One or more of the healthcare devices 130A-F that provide medications, e.g. that provide access to medications or that administer medications, may transmit signals, such as replenishment signals, to the PIS 120 when the medications need to be replenished. For example, an intravenous (IV) pump may transmit a replenishment signal when an IV bag that is being administered to a patient needs to be replenished. Similarly, an automated dispensing machine may transmit a replenishment signal when one or more of the medications distributed by the automated dispensing machine are running low.

The electronic devices 140A-B may be any electronic devices such as laptop or desktop computers, mobile phones, personal digital assistants ("PDAs"), tablet computers, televisions or other displays, or other appropriate computing devices that can be used to display user interfaces that facilitate with, e.g., picking component medications for ordered medications and/or preparing ordered medications. For example, the electronic device 140A that is located in the medication storage area may display a queue to facilitate with retrieving, or picking, medications from inventory for received orders in a manner that substantially minimizes waste, while the electronic device 140B that is located in the medication preparation area may display a queue to facilitate with preparing ordered medications in a manner that substantially minimizes waste.

In the example of FIG. 1, the electronic devices 140A-B are depicted as desktop computers; however, the electronic devices 140A-B may be any of the aforementioned electronic devices, and/or any other electronic devices, e.g. The electronic devices 140A-B may include a processor and/or a memory. The electronic devices 140A-B may include input devices that may be used to select or identify component medications and/or containers that contain component medications, e.g. by scanning a label attached to a container. The input devices may include, e.g., bar code scanners, radio frequency identification (RFID) readers, or generally any devices that can recognize or identify a component medication, a container that contains a component medication, and/or a container that will be used to store an ordered medication.

For explanatory purposes, the electronic device 140A is described herein as being located in a medication storage area and the electronic device 140B is described herein as being located in a medication preparation area; however, the electronic devices 140A-B may be portable devices, e.g. a tablet device or a mobile phone, that a healthcare professional may carry in and out of the medication storage area and/or the medication preparation area. The medication storage area and/or the medication preparation area may be proximally located within a pharmacy of a healthcare facility. Alternatively, or in addition, the medication storage area and the medication preparation area may be disparately located within, or outside of, the healthcare facility. In one or more implementations, the healthcare facility may include multiple medication storage areas, one or more of which may include the electronic device 140A, and/or multiple medication preparation areas, one or more of which may include the electronic device 140B.

In operation, one or more orders for medications may be received by the PIS 120, such as from the POE system 110, or from one of the healthcare devices 130A-F, e.g. in the form of a replenishment signal. An order may indicate at least one component medication, such as cefazolin, vancomycin, norepinephrine, saline solution, etc., along with an amount of the component medication to be used to prepare the medications. In one or more embodiments, the orders for medications may include orders for IV bags. The PIS 120 may transmit the orders to the electronic device 140A that is located in the medication storage area, such that the component medications of the orders can be picked e.g. retrieved, from the medication storage area, e.g. by a healthcare professional.

In one or more embodiments, the healthcare facility may utilize anticipatory batching for fast moving compounds or components. For example, a determined amount of a medication that includes a particular compound or component may be prepared as an anticipatory batch, e.g. irrespective of whether any orders have been received for the medication. The anticipatory batch of the medication may be associated with one or more periodic automatic replenishment (PAR) levels. If the prepared amount of the medication, e.g. from the anticipatory batch, falls below a PAR level, a system, such as the PIS 120, may generate one or more orders for the medication, e.g. an "auto-reorder" based on the PAR levels set, and the one or more orders may be provided to the PIS 120, e.g. along with orders received from the POE 110 and/or from one or more of the healthcare devices 130A-F.

The electronic device 140A that is located in the medication storage area may aggregate the received orders into batches, or groups, e.g. based on the component medications that are indicated by each order. For example, the electronic device 140A may batch the orders such that orders that have a common (e.g., the same) component medication are picked together. After batching the orders, e.g. based on the component medications, the electronic device 140A may select the first batch of orders and determine the containers from inventory that should be picked to prepare the first batch of orders in a manner that minimizes wasted component medications. The containers may include vials, bags, bottles, packages, or generally any container that can store a component medication. In one or more embodiments, the steps of batching the orders and determining the containers to be retrieved from inventory to prepare a batch of orders may be performed by the PIS 120, and/or another server system. The PIS 120 may then transmit the batches, along with the amount of component medications to be retrieved for each batch and/or the containers to be retrieved from inventory for each batch, to the electronic device 140A. An example process for batching the orders is discussed further below with respect to FIG. 2.

The electronic device 140A may determine a first batch of orders and may provide an indication of the component medications needed to prepare the first batch, the amount of the component medications that needs to be retrieved for the first batch, and the containers from inventory that should be retrieved for the first batch. For example, the electronic device 140A may display a user interface, such as the user interface discussed below with respect to FIG. 4, to facilitate the healthcare professional with picking the component medications for the first batch. The healthcare professional may retrieve the containers from the inventory of the medication storage area for preparing the first batch. For example, the healthcare professional may identify each container that is retrieved from inventory, e.g. by scanning the containers with a bar code scanner. The electronic device 140A may transmit indications of the scanned containers to the PIS 120 and the PIS 120 may store an indication that the containers are being removed from the inventory of the medication storage area and being delivered to a temporary inventory of a medication preparation area. The containers may then be delivered to the medication preparation area for preparation of the first batch of orders.

Once the containers containing the component medications for the first batch of orders are delivered to the medication preparation area, the electronic device 140B (that is located in the medication preparation area) receives an indication of the first batch of orders. The electronic device 140B may display, e.g. to a healthcare professional who will be preparing the first batch of orders, a user interface that includes a queue that lists the first batch of orders. For example, the electronic device 140B may display the user interface that is discussed further below with respect to FIG. 5. In one or more embodiments, the electronic device 140B may order the queue such that the orders that will be prepared with a common component medication are displayed adjacently in the queue.

The electronic device 140B may receive an indication that the healthcare professional has initiated preparation of an order listed in the queue, and/or that the healthcare professional has selected an order listed in the queue. Upon receiving the indication, the electronic device 140B determines whether there are any other orders listed in the queue that will be prepared using the component medication of the order that is currently being prepared. If the electronic device 140B determines that any such orders are listed in the queue, the electronic device 140B may notify the healthcare professional of the orders and/or the electronic device 140B may re-order the queue, if necessary, such that the orders are listed in the queue adjacent to the order currently being prepared. In this manner, orders that are prepared using the same component medication can be prepared together, thereby minimizing any excess amount of component medication that is wasted. An example process for aggregating orders based on common component medications is discussed further below with respect to FIG. 3.

Figure 2:
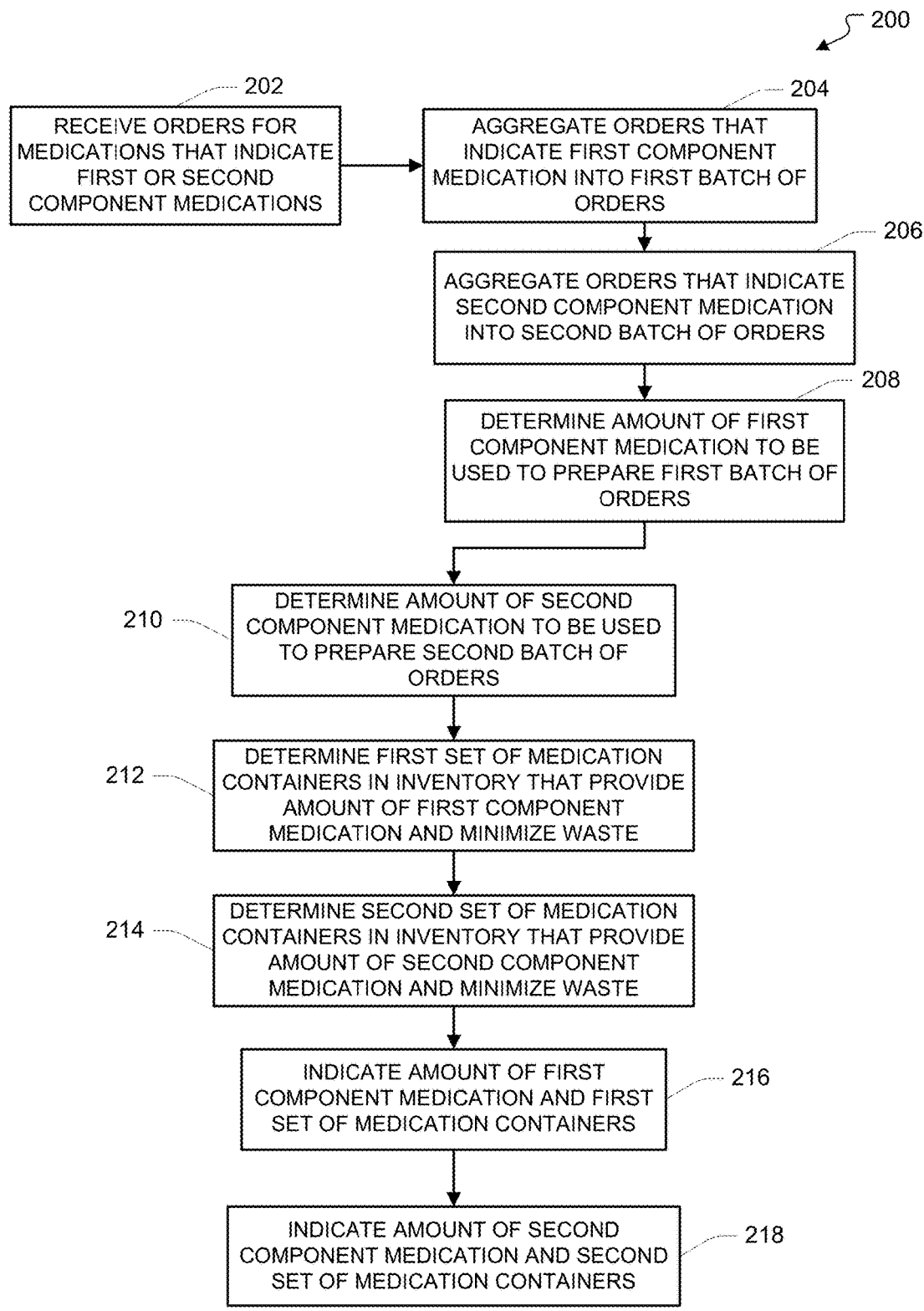
FIG. 2 illustrates a flow diagram of an example process for a system for component based aggregation of medication orders in accordance with one or more embodiments.

FIG. 2 illustrates a flow diagram of an example process 200 for a system for component based aggregation of medication orders in accordance with one or more embodiments. For explanatory purposes, the example process 200 is described herein with reference to the electronic device 140A of FIG. 1; however, the example process 200 is not limited to the electronic device 140A of the example hospital network environment 100 of FIG. 1. For example, one or more blocks of the example process 200 may be performed by the PIS 120 or another server system. Further for explanatory purposes, the blocks of the example process 200 are described herein as occurring in serial fashion, or linearly. However, multiple blocks of the example process 200 may occur in parallel. In addition, the blocks of the example process 200 need not be performed in the order shown and/or one or more of the blocks of the example process 200 need not be performed.

In block 202, the electronic device 140A in the medication storage area receives orders for medications, such as from the PIS 120. Alternatively, or in addition, the orders may be received from the POE system 110 and/or from one or more of the healthcare devices 130A-F. An order for a medication may indicate one or more component medications that are used to prepare the medication, such as cefazolin, vancomycin, saline solution, etc., and an amount, or a range of amounts, of each component medication that is used to prepare the medication. At least some of the received orders may indicate at least one of a first component medication or a second component medication. In block 204, the electronic device 140A aggregates the orders that indicate the first component medication into a first batch of orders. In block 206, the electronic device 140A aggregates the orders that indicate the second component medication into a second batch of orders.

In block 208, the electronic device 140A determines an amount of the first component medication that will be used to prepare the first batch of orders. For example, the electronic device 140A may add the amounts of the first component medication indicated by each of the orders of the first batch to determine the amount of the first component medication that will be used to prepare the first batch of orders. In block 210, the electronic device 140A determines an amount of the second component medication that will be used to prepare the second batch of orders. For example, the electronic device 140A may add the amounts of the second component medication indicated by each of the orders of the second batch to determine the amount of the second component medication that will be used to prepare the second batch of orders.

In block 212, the electronic device 140A determines a first set of medication containers in the inventory of the medication storage area that can provide the determined amount of the first component medication and minimize waste. For example, the electronic device 140A may determine a first set of containers such that the containers collectively contain at least the determined amount of the first component medication and such that the containers minimize any amount of the first component medication that is in excess of the determined amount. Thus, if the determined amount of the first component medication is 1400 milliliters (mL), and there are containers that contain the first component medication in sizes that include, e.g., 300 mL, 750 mL, and 1000 mL, the electronic device 140A may determine that two of the 750 mL containers should be retrieved, rather than, e.g., two of the 1000 mL containers, since the two 750 mL containers only result in an excess amount of 100 mL, while the two 1000 mL containers would result in an excess amount of 600 mL. Thus, picking the two 750 mL containers, rather than the two 1000 mL containers, may reduce the amount of the first medication component that is wasted by up to 500 mL.

In one or more embodiments, the electronic device 140A may determine whether any prepared medications that include the first component medication have been returned to the medication storage area, and/or to the pharmacy. If the electronic device 140A determines that any prepared medications that include the first component medication have been returned, the electronic device 140A determines whether the returned medications can be used to prepare any of the orders of the first batch. For example, the electronic device 140A may determine whether the returned medications have expired, or whether the returned medications will expire before they can be used to prepare and administer one of the orders of the first batch. If the electronic device 140A determines that any of the prepared medications can be used to prepare an order from the first batch, the electronic device 140A may prioritize the selection of the returned medications over any component medications in the storage area, e.g., since the returned medications are likely to expire sooner than the stored component medications.

In block 214, the electronic device 140A determines a second set of medication containers in the inventory of the medication storage area that can provide the determined amount of the first component medication and minimize waste. For example, the electronic device 140A may determine a second set of containers such that the containers collectively contain at least the determined amount of the second component medication and such that the containers minimize any amount of the second component medication that is in excess of the determined amount, as discussed above with respect to the first component medication.

In block 216, the electronic device 140A indicates the amount of the first component medication that will be used to prepare the first batch of orders and the determined first set of the medication containers, such as to the healthcare professional who is picking, or retrieving, the first component medication from the medication storage area. For example, the electronic device 140A may display the user interface discussed below with respect to FIG. 4 to the healthcare professional. In one or more embodiments, the electronic device 140A may only provide the healthcare professional with an indication of the first component medication and the amount of the first component medication that will be used to prepare the first batch of orders. The healthcare professional may pick the indicated first set of containers from inventory and may use a scanning device associated with the electronic device 140A to scan the picked first set of containers. The electronic device 140A may transmit an indication of the scanned first set of containers to the PIS 120. The PIS 120 may associate the scanned first set of containers with the first batch of orders and the PIS 120 may move the scanned first set of containers from the inventory of the medication storage area to a temporary inventory of the medication preparation area.

In block 218, the electronic device 140A indicates the amount of the second component medication that will be used to prepare the second batch of orders and the determined second set of the medication containers, such as to the healthcare professional who is picking, or retrieving, the second component medication from the medication storage area. For example, the electronic device 140A may display the user interface discussed below with respect to FIG. 4 to the healthcare professional. In one or more embodiments, the electronic device 140A may only provide the healthcare professional with an indication of the second component medication and the amount of the second component medication that will be used to prepare the second batch of orders. The healthcare professional may pick the indicated second set of containers from inventory and may use a scanning device associated with the electronic device 140A to scan the picked second set of containers. The electronic device 140A may transmit an indication of the scanned second set of containers to the PIS 120. The PIS 120 may associate the scanned second set of containers with the second batch of orders and the PIS 120 may move the scanned second set of containers from the inventory of the medication storage area to a temporary inventory of the medication preparation area. The retrieved component medications for the first and/or second batch of orders may be delivered to the medication preparation area.

In one or more embodiments, the electronic device 140A may aggregate the first batch of orders, and may deliver the first batch of orders to the medication preparation area, separately from the second batch of orders. For example, each batch of orders may be assigned to be prepared by a particular healthcare professional that is located in a particular medication preparation area. Thus, the first batch of orders may be aggregated, picked, and delivered to a medication preparation area associated with a first healthcare professional, and the second batch of orders may be aggregated, picked, and delivered to a second medication preparation area associated with a second healthcare professional. Alternatively, or in addition, multiple batches of orders may be combined together for delivery to a medication preparation area and for preparation by a single healthcare professional. For example, if there is not a sufficient number of ordered medications that share a common component medication, orders for different component medications may be batched together.

One of the healthcare devices 130A-F determines whether more than one item, or group of items, were identified as being able to properly fulfill the order. If the one of the healthcare devices 130A-F determines that there is only one item that meets the criteria the one of the healthcare devices 130A-F dispenses the item determined.

If the one of the healthcare devices 130A-F determines that there is more than one item that satisfies the criteria the one of the healthcare devices 130A-F dispenses the item that will result in the least amount of wasted medication, e.g. the item that has an amount that is closest to the amount to be administered. For example, if the amount to be administered is 7 mg of morphine for a 2 mg-10 mg order, and the one of the healthcare devices 130A-F contains an 8 mg vial and a 9 mg vial, the one of the healthcare devices 130A-F dispenses the 8 mg vial since it will only result in 1 mg of waste as opposed to the 2 mg of waste that would result from dispensing the 9 mg vial. Alternatively, or in addition, if more than one item meets the criteria and has the same dosage or in the same dosage form/group, the one of the healthcare devices 130A-F may dispense the item with the lowest configured dispense order. In one or more embodiments, the dispense order of the items may be configured by a pharmacy.

Figure 3:
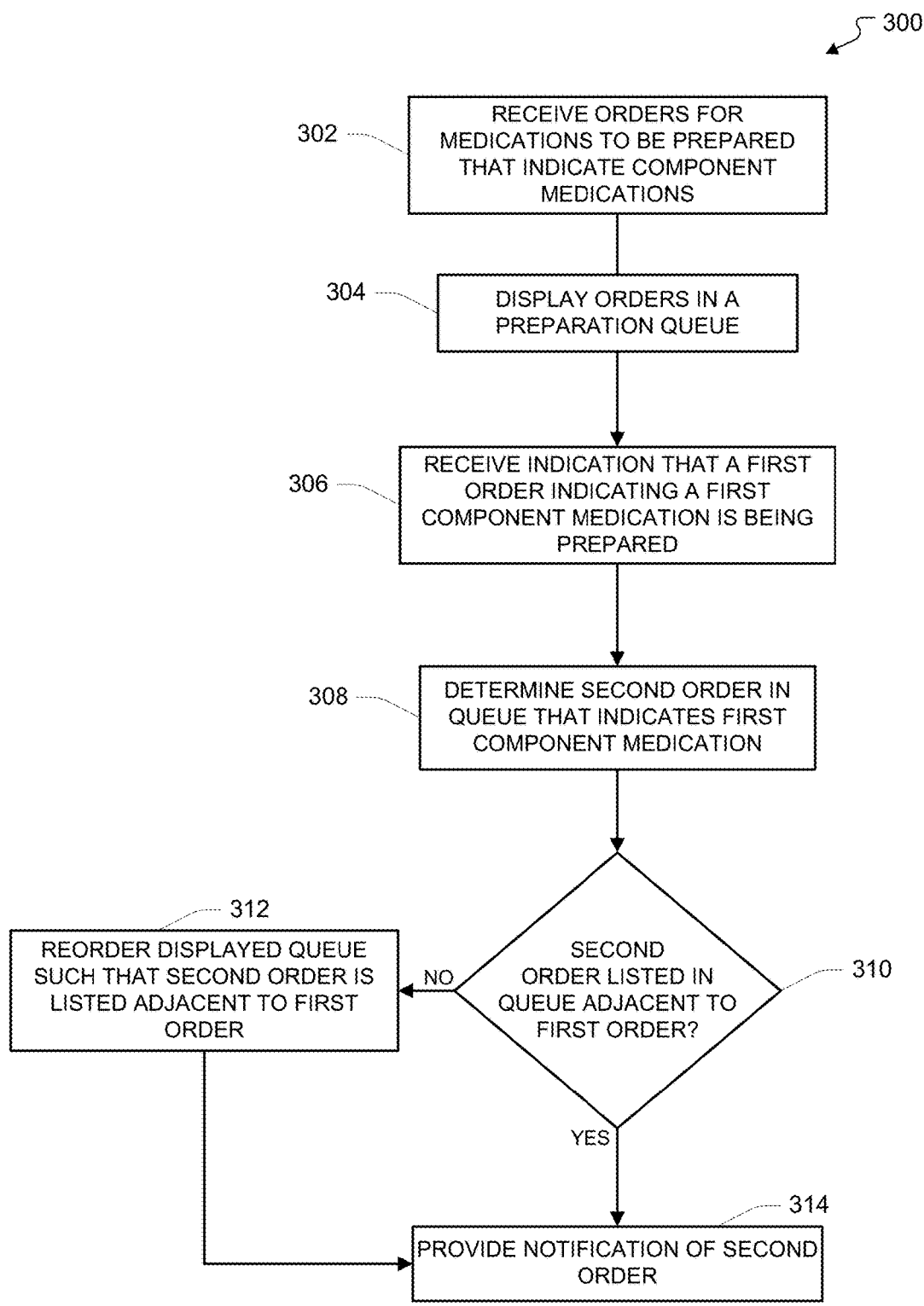
FIG. 3 illustrates a flow diagram of an example process for a system for component based aggregation of medication orders in accordance with one or more embodiments.

FIG. 3 illustrates a flow diagram of an example process 300 for a system for component based aggregation of medication orders in accordance with one or more embodiments. For explanatory purposes, the example process 300 is described herein with reference to the electronic device 140B of FIG. 1; however, the example process 300 is not limited to the electronic device 140B of the example hospital network environment 100 of FIG. 1. For example, one or more blocks of the example process 300 may be performed by the PIS 120 or another server system. Further for explanatory purposes, the blocks of the example process 300 are described herein as occurring in serial fashion, or linearly. However, multiple blocks of the example process 300 may occur in parallel. In addition, the blocks of the example process 300 need not be performed in the order shown and/or one or more of the blocks of the example process 300 need not be performed.

In block 302, the electronic device 140B that is located in the medication preparation area receives orders for medications to be prepared, where the orders indicate component medications, and amounts thereof, to be used to prepare the ordered medications. For example, after the component medications for a batch of orders have been picked and scanned, the PIS 120 may transmit an indication of the batch of orders to the medication preparation area. In one or more implementations, a healthcare facility may not implement the process described above with respect to FIG. 2 when picking the orders. Thus, the orders received by the electronic device 140B may not be aggregated based on a common component medication.

In block 304, the electronic device 140B may display the received orders in a queue. The electronic device 140B may display the queue on a display that is attached to the electronic device 140B, such as a screen of the electronic device 140B, or on a remote display that is communicatively coupled to the electronic device 140B, such as a display screen hanging on a wall in the medication preparation area. For example, the electronic device 140B may display the user interface that is discussed further below with respect to FIG. 5 to the healthcare professional.

In block 306, the electronic device 140B receives an indication that an order for a medication that includes a first component medication is being prepared. For example, the indication may be generated when the healthcare professional selects one of the orders that are listed in the queue, e.g. using a human interface device of the electronic device 140B, such as a mouse, a keyboard, or a touch screen. Alternatively, or in addition, the indication may be generated when the healthcare professional uses a scanning device, which is communicatively coupled to the electronic device 140B, to scan a container that will be used to store the medication when the medication is prepared, e.g. the container may include a label, a bar code, or any other detectable identifier.

In block 308, the electronic device 140B determines a second order listed in the queue that indicates the first component medication. For example, if the first component medication is cefazolin, the electronic device 140B may determine another order for a medication that includes cefazolin. In block 310, the electronic device 140B determines whether the second order that indicates the first component medication is listed in the queue adjacent to the first order that indicates the first component medication, e.g. such that the first and second orders will be prepared sequentially and/or in aggregate. If, in block 310, the electronic device 140B determines that the second order that indicates the first component medication is not listed in the queue adjacent to the first order that indicates the first component medication, the electronic device 140B moves to block 312. In block 312, the electronic device 140B reorders the displayed queue such that the second order is displayed in the queue adjacent to the first order.

If, in block 310, the electronic device 140B determines that the second order is listed in the queue adjacent to the first order, the electronic device 140B moves to block 314. In block 314, the electronic device 140B provides a notification to the healthcare professional of the second order. For example, the electronic device 140B may display a pop-up window that alerts the healthcare professional to the second order. In this manner, the electronic device 140B facilitates the healthcare professional with preparing the first and second orders, that both indicate the first component medication, in aggregate.

Figure 4:
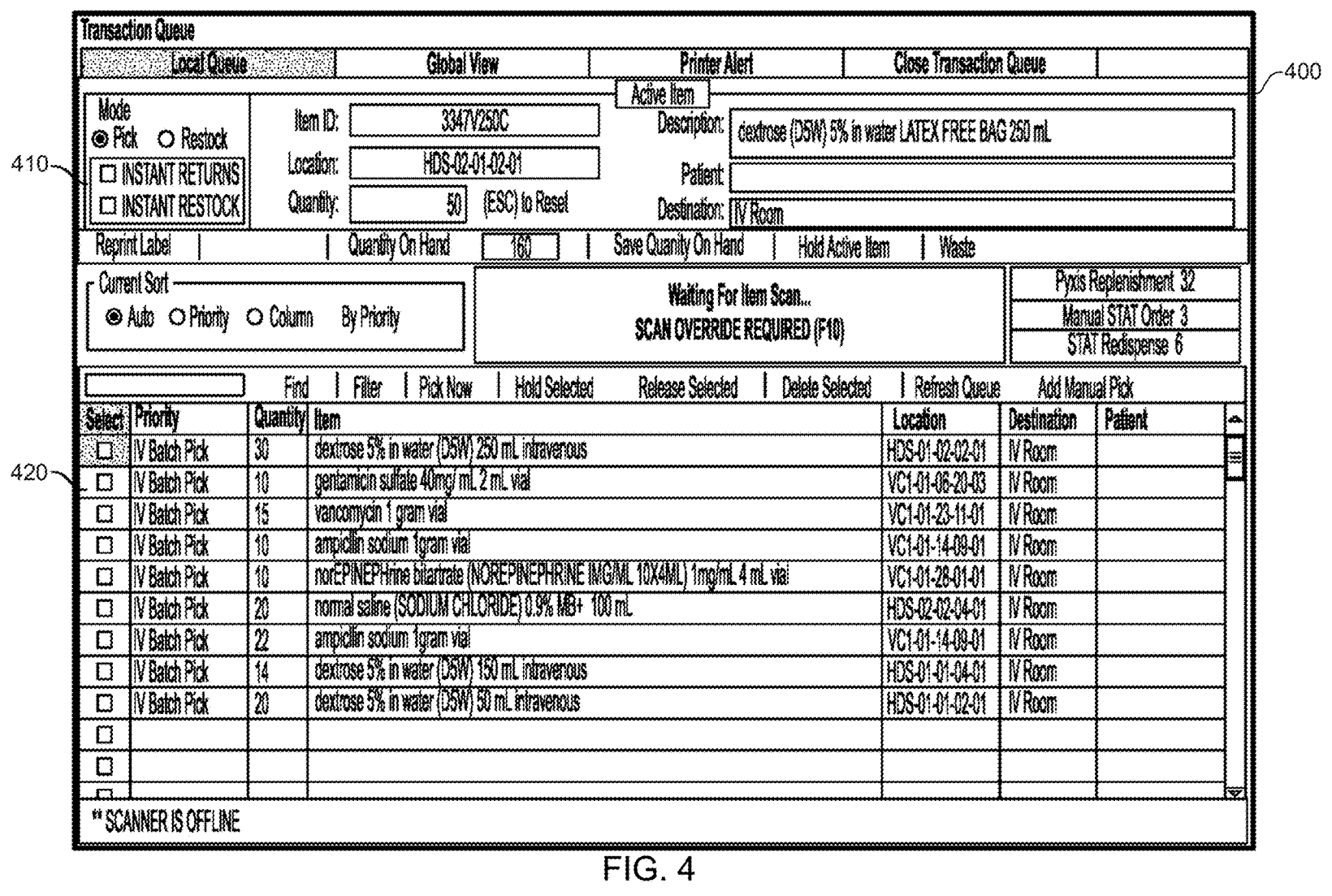

FIG. 4 illustrates an example user interface 400 that may be utilized in a system for component based aggregation of medication orders in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The example user interface 400 includes an information display area 410, and a batch display area 420. The information display area 410 may display information regarding a selected order for a medication and/or a selected component medication. The batch display area 420 may display batches of orders for medications that have been grouped together, e.g., based on a common component medication. In operation, the user interface 400 may be displayed on the electronic device 140A in the medication storage area, e.g. to facilitate a healthcare professional with picking component medications in a manner that minimizes any wasted amounts of the component medications.

Figure 5:
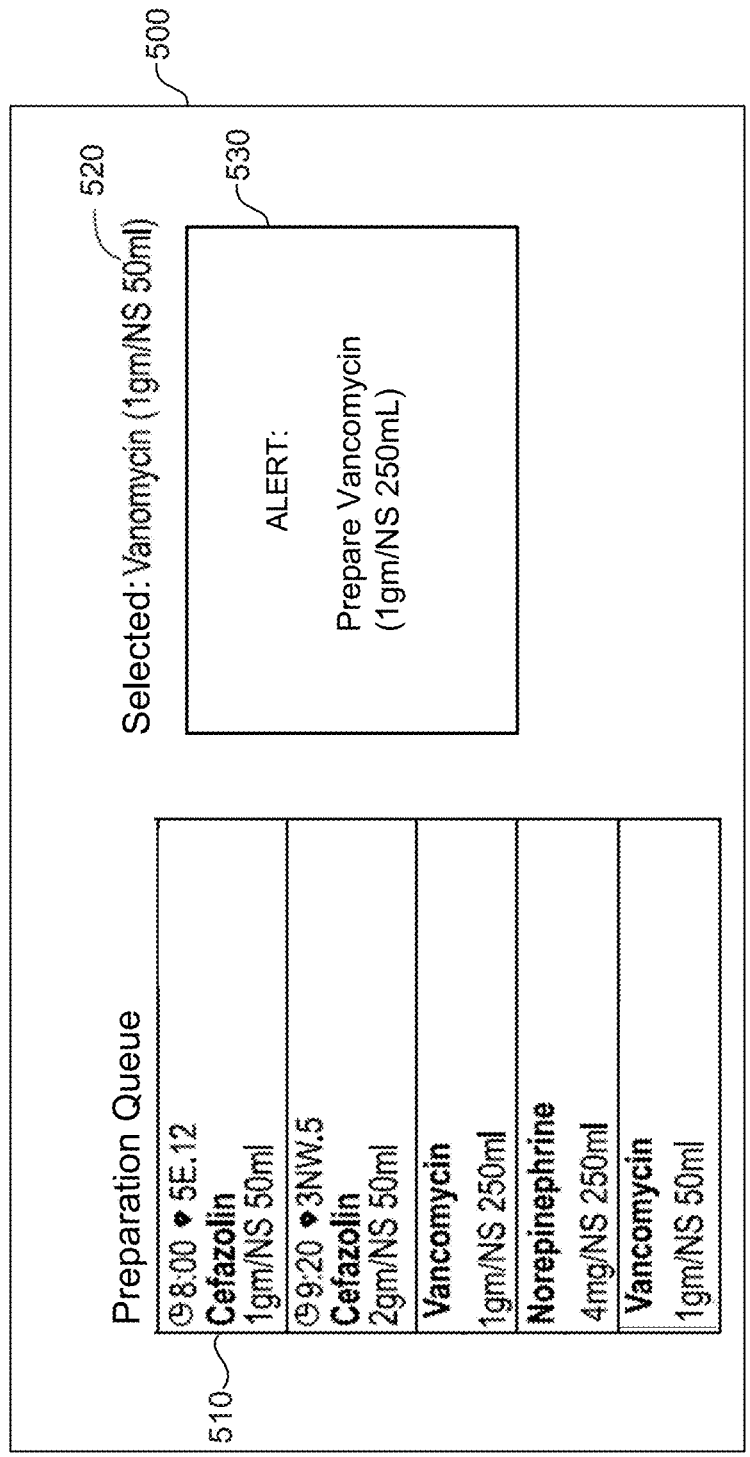
FIG. 5 illustrates an example user interface that may be utilized in a system for component based aggregation of medication orders in accordance with one or more embodiments.

FIG. 5 illustrates an example user interface 500 that may be utilized in a system for component based aggregation of medication orders in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The user interface 500 includes a preparation queue 510, a selected order field 520, and an information display area 530. The preparation queue 510 lists the orders that need to be prepared, e.g. by a healthcare professional. The selected order field 520 may display an order that was selected by a healthcare professional, or an order that the healthcare professional has started to prepare. The information display area 530 may display information to the healthcare professional that is relevant to the selected order.

In operation, the user interface 500 may be displayed on the electronic device 140B that is located in the medication preparation area, e.g. to facilitate a healthcare professional with preparing ordered medications in a manner that minimizes any wasted amounts of component medications. For example, when the healthcare professional selects an order from the preparation queue 510, or otherwise indicates that the preparation of an order listed in the queue has begun, e.g. by scanning a label or container associated with the order, the user interface 500 displays the selected order in the selected order field 520. In addition, if there are any other orders in the preparation queue 510 that indicate the component medication that is used to prepare the selected order, e.g. in FIG. 5 "Vancomycin," the user interface 500 displays the additional orders in the information display area 530. In this manner, the healthcare professional can prepare the orders in aggregate, which may minimize the amount of the component medication that is wasted, e.g. as opposed to if the orders are prepared separately.

Alternatively, or in addition, the preparation queue 510 may be reordered such that the selected order, and any other orders that indicate the component medication of the selected order, are displayed at the top of the queue. Thus, in FIG. 5, the preparation queue 510 may be reordered such that the "Vancomycin 1 gm/NS 50 mL" order is displayed first in the preparation queue 510, and the "Vancomycin 1 gm/NS 250 mL" order is displayed second in the preparation queue 510.

Figure 6:
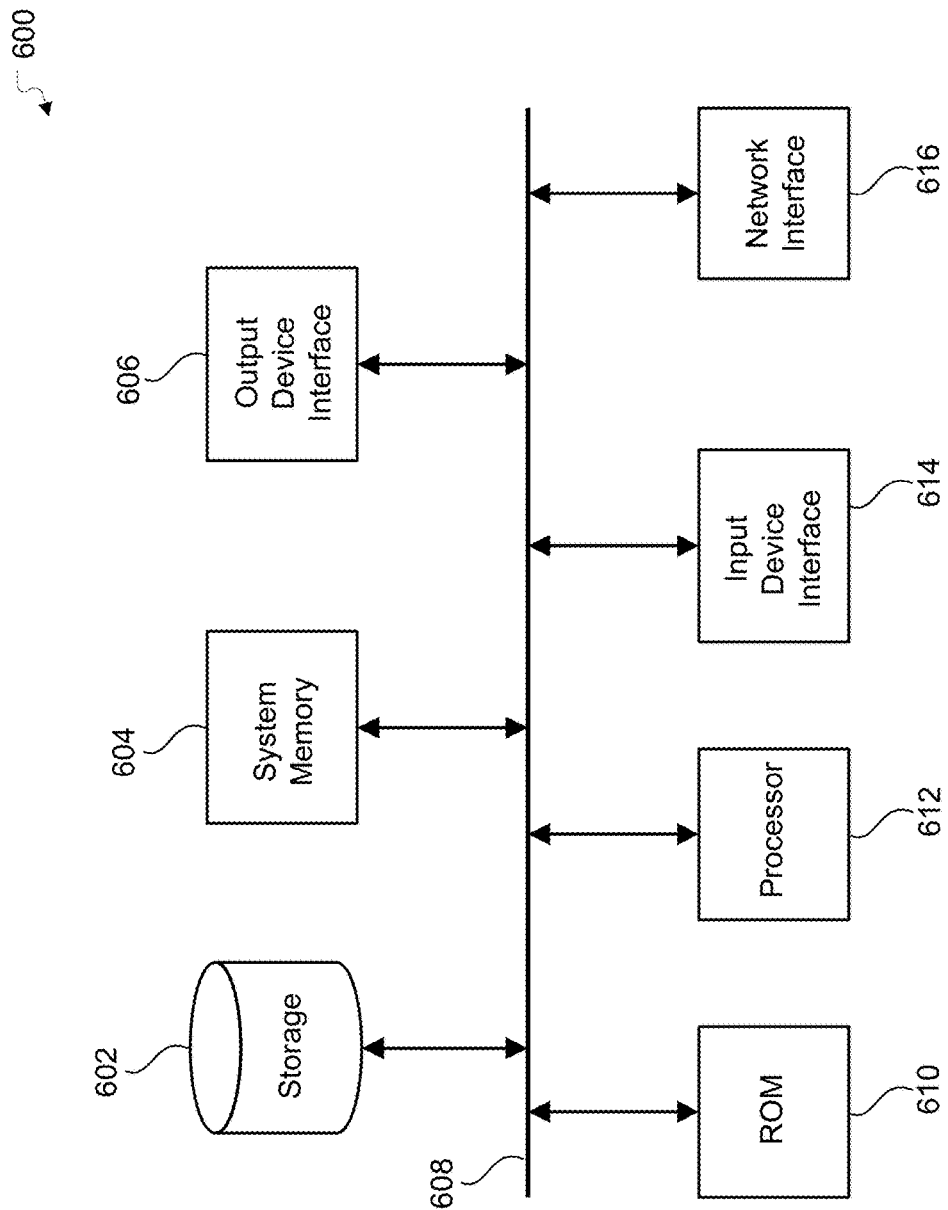
FIG. 6 conceptually illustrates an electronic system with which one or more embodiments of the subject technology may be implemented.

FIG. 6 conceptually illustrates electronic system 600 with which one or more embodiments of the subject technology may be implemented. Electronic system 600, for example, may be, or may be a part of, the POE system 110, the PIS 120, the healthcare devices 130A-F, the electronic device 140A that is located in the medication storage area, the electronic device 140B that is located in the medication preparation area, a desktop computer, a laptop computer, a tablet computer, a phone, a personal digital assistant (PDA), or generally any electronic device that transmits signals over a network. Such an electronic system includes various types of computer readable media and interfaces for various other types of computer readable media. Electronic system 600 includes bus 608, processing unit(s) 612, system memory 604, read-only memory (ROM) 610, permanent storage device 602, input device interface 614, output device interface 606, and network interface 616, or subsets and variations thereof Bus 608 collectively represents all system, peripheral, and chipset buses that communicatively connect the numerous internal devices of electronic system 600. In one or more embodiments, bus 608 communicatively connects processing unit(s) 612 with ROM 610, system memory 604, and permanent storage device 602. From these various memory units, processing unit(s) 612 retrieves instructions to execute and data to process in order to execute the processes of the subject disclosure. The processing unit(s) can be a single processor or a multi-core processor in different embodiments.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. One or more embodiments of the subject disclosure use a mass-storage device (such as a magnetic or optical disk and its corresponding disk drive) as permanent storage device 602.

Other embodiments use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such as random access memory. System memory 604 stores any of the instructions and data that processing unit(s) 612 needs at runtime. In one or more embodiments, the processes of the subject disclosure are stored in system memory 604, permanent storage device 602, and/or ROM 610. From these various memory units, processing unit(s) 612 retrieves instructions to execute and data to process in order to execute the processes of one or more embodiments.

Bus 608 also connects to input and output device interfaces 614 and 606. Input device interface 614 enables a user to communicate information and select commands to the electronic system. Input devices used with input device interface 614 include, for example, alphanumeric keyboards, pointing devices (also called "cursor control devices"), scanning devices, such as bar code scanners, RFID scanners, or generally any device that can receive input. Output device interface 606 enables, for example, the display of images generated by electronic system 600. Output devices used with output device interface 606 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more embodiments may include devices that function as both input and output devices, such as a touch screen. In these embodiments, feedback provided to the user can be any form of sensory feedback, such as visual feedback, auditory feedback, or tactile feedback; and input from the user can be received in any form, including acoustic, speech, or tactile input.

Finally, as shown in FIG. 6, bus 608 also couples electronic system 600 to a network (not shown) through network interface 616. In this manner, the computer can be a part of a network of computers (such as a local area network ("LAN"), a wide area network ("WAN"), or an Intranet, or a network of networks, such as the Internet. Any or all components of electronic system 600 can be used in conjunction with the subject disclosure.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more embodiments, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more embodiments, the computer readable media is non-transitory computer readable media, computer readable storage media, or non-transitory computer readable storage media.

In one or more embodiments, a computer program product (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more embodiments are performed by one or more integrated circuits, such as application specific integrated circuits (ASICs) or field programmable gate arrays (FPGAs). In one or more embodiments, such integrated circuits execute instructions that are stored on the circuit itself Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more embodiments, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A method for component-based aggregation of medication orders comprising:
 receiving, by one or more computing devices, a replenishment signal for an auto-reorder medication order;
 aggregating, from the auto-reorder medication order and a plurality of medication orders, by the one or more computing devices based on receiving the replenishment signal and without user intervention, a first batch of medication orders and a second batch of medication orders, wherein at least one of the plurality of medication orders indicates a first component medication to be formulated into a first medication and at least one of the plurality of medication orders indicates a second component medication to be formulated into a second medication;

determining, by the one or more computing devices in response to the aggregating, a first amount of the first component medication to be used to formulate the first batch, and a second amount of the second component medication to be used to formulate the second batch;

determining, by the one or more computing devices in response to determining the first amount, a first plurality of medication containers that contain, in aggregate, at least the first component medication in an amount greater than or equal to the first amount, and a second plurality of medication containers that contain, in aggregate, at least the the second component medication in an amount greater than or equal to the second amount;

providing for display, by the one or more computing devices, an indication of at least a first subset of the first plurality of medication containers being available for selection and an indication of at least a second subset of the second plurality of medication containers being available for selection;

receiving, by the one or more computing devices, an indication that the first subset or the second subset was selected for dispense; and controlling, by one or more computing devices, a healthcare device to dispense the first amount of the first component medication or the second amount of the second component medication from the selected first plurality of medication containers or the selected second plurality of medication containers, respectively.

2. The method of claim 1, wherein indicating the first amount of the first component medication and the second amount of the second component medication comprises displaying the first amount of the first component medication and the second amount of the second component medication to a healthcare professional responsible for picking the first amount of the first component medication and the second amount of the second component medication from a medication storage area.

3. The method of claim 1, wherein an aggregate amount of the second component medication in the second plurality of medication containers is greater than the second amount of the second component medication.

4. The method of claim 3, wherein the second subset of the second plurality of medication containers is selected to minimize a second excess amount by which the second aggregate amount of the second medication exceeds the second amount such that the second excess amount is less than a smallest container size of the second plurality of medication containers.

5. The method of claim 3, wherein displaying a first indication of the first subset of the first plurality of medication containers comprises displaying the first indication for selection by a healthcare professional responsible for picking the first amount of the first component medication from a medication storage, and wherein displaying a second indication of the second subset of the second plurality of medication containers comprises displaying the second indication for selection by a healthcare professional responsible for picking the second amount of the second component medication from the medication storage.

6. The method of claim 5, wherein indicating the first amount of the first component medication and the second amount of the second component medication comprises generating a queue that lists the first batch of medication orders and the second batch of medication orders, wherein the first batch of medication orders are listed adjacently in the queue prior to the second batch of medication orders.

7. The method of claim 6, further comprising displaying, in an area where the plurality of medication orders are formulated, the queue that lists the first and second batches of medication orders.

8. The method of claim 7, wherein the area where the plurality of medication orders are formulated comprises a clean room.

9. The method of claim 7, further comprising receiving a selection of a medication order listed in the queue, wherein the selected medication order indicates the second component medication.

10. The method of claim 9, further comprising reordering the queue such that the second batch of medication orders that indicate the second component medication are listed adjacent to the selected medication order and prior to the first batch of medication orders.

11. The method of claim 9, further comprising displaying, separately from the queue, the second batch of medication orders that indicate the second component medication.

12. The method of claim 1, further comprising:

receiving a replenishment order from the healthcare device, the healthcare device comprising an infusion device or an automated dispensing machine, wherein the first batch of medication orders is aggregated from the replenishment order received from the healthcare device and another order received from an order entry device different than the healthcare device.

13. The method of claim 12, wherein the order entry device is at least part of a physician order entry system that receives order information via user input.

14. The method of claim 1, wherein at least one of the plurality of medication orders comprises an intravenous medication order.

15. A system for component-based aggregation of medication orders, the system comprising:

one or more processors; and a memory including instructions that, when executed by the one or more processors, cause the one or more processors to:

display a queue listing a plurality of medication orders to be prepared, each of the plurality of medication orders indicating one of a plurality of component medications, the plurality of medication orders including a first auto-reorder medication order for a first medication;

receive a selection of a first medication order of the plurality of medication orders listed in the queue, wherein the first medication order of the plurality of medication orders indicates a first component medication of the plurality of component medications;

determine a second medication order of the plurality of medication orders listed in the queue that indicates the first component medication of the plurality of component medications;

reorder the displayed queue such that the second medication order of the plurality of medication orders is listed adjacent to the first medication order of the plurality of medication orders;

determine a first amount, the first amount being an amount of the first component medication to be used to formulate a first batch of medication orders including the first medication order and the second medication order;

determine, from a first plurality of medication containers that each contains the first component medication, a first subset of the first plurality of medication containers that contain, in aggregate, a first aggregate amount of the first component medication greater than or equal to the first amount, the first subset including a first excess amount by which the first aggregate amount exceeds the first amount; and control a healthcare device to dispense the first amount of the first component medication from the first plurality of medication containers.

16. The system of claim 15, wherein the instructions, when executed by the one or more processors, further cause the one or more processors to:

determine the first subset such that the first aggregate amount of the first component medication is greater than the first amount of the first component medication, and such that the first excess amount is less than a smallest container size of the first plurality of medication containers.

17. The system of claim 15, wherein the instructions, when executed by the one or more processors, further cause the one or more processors to:

display the queue that lists the plurality of medication orders on a display in a clean room where the plurality of medication orders are prepared; and receive the selection of the first medication order of the plurality of medication orders listed in the queue from a device associated with a healthcare professional who is preparing the first medication order of the plurality of medication orders.

18. A computer implemented method comprising operations initiated by one or more computing devices, the operations comprising:

generating a first auto-reorder medication order for a first medication based on an anticipatory batch of the first medication;

generating a second auto-reorder medication order for the first medication when the anticipatory batch falls below a target replenishment level, wherein a plurality of medication orders includes the first auto-reorder medication order and the second auto-reorder medication order, each of the plurality of medication orders indicating one of a plurality of component medications;

receiving an indication that a medication order of the plurality of medication orders is being prepared by a healthcare professional, wherein the medication order of the plurality of medication orders indicates a first component medication of the plurality of component medications;

determining other medication orders of the plurality of medication orders that indicate the first component medication of the plurality of component medications;

displaying one or more of the other medication orders of the plurality of medication orders that indicate the first component medication of the plurality of component medications;

determining a first amount, the first amount being an amount of the first component medication to be used to formulate a first batch of medication orders including the medication order and the other medication orders of the plurality of medication orders that indicate the first component medication;

determine, from a first plurality of medication containers that each contains the first component medication, a first subset of the first plurality of medication containers that contain, in aggregate, a first aggregate amount of the first component medication greater than or equal to the first amount;

receiving an indication that the first subset was selected for dispensing, the first subset including a first excess amount by which the first aggregate amount exceeds the first amount; and controlling a healthcare device to dispense the first amount of the first component medication from the first plurality of medication containers.

19. The method of claim 18, wherein the operations further comprise:

determining the first subset such that the first aggregate amount of the first component medication is greater than the first amount of the first component medication, and such that the first excess amount is less than a smallest container size of the first plurality of medication containers.

20. The method of claim 19, wherein the indication indicates that the healthcare professional scanned a bar code associated with the first component medication of the plurality of component medications.

* * * * *